Oct. 15, 1963 M. C. RICH Plant Pat. 2,289
GLADIOLUS PLANT
Filed June 25, 1962
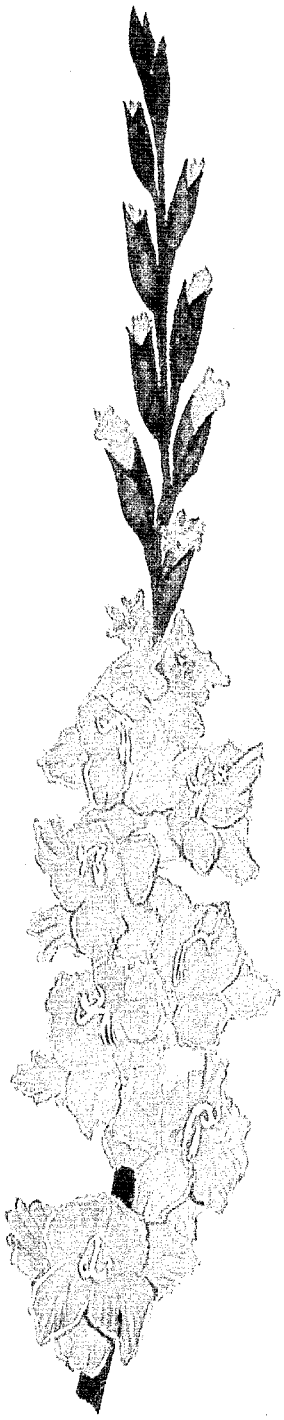
INVENTOR
Marion C. Rich
By: Lamont Johnston
ATTORNEY United States Patent Office Plant Pat. 2,289
Patented Oct. 15, 1963

2,289
GLADIOLUS PLANT

Marion C. Rich, Marion, N.Y., assignor to Selected Glads, Inc., New Albany, Ind., a corporation of Tennessee Filed June 25, 1962, Ser. No. 205,139
1 Claim. (Cl. Plt.—85)

My present invention relates to a new and improved variety of gladiolus plant and is notable particularly for its Chinese Yellow picotee edging on a velvety, deep red background.

To the best of my knowledge, this new variety is the result of a cross between the varieties Fifth Avenue (unpatented) and Twinkles (unpatented), Fifth Avenue being the seed parent and Twinkles the pollen parent. Hand cross pollination was done by me in my garden at Marion, New York, but no precaution was taken to prevent admixture of other varieties by bees or insects.

The new variety has been asexually reproduced by me in New York by natural increase from cormels through several generations and its characteristics have proven to be permanently fixed.

The illustration, made a part of this application, shows a single bloom spike of this variety, reduced in size, and is as nearly true to color as it is possible to depict. The illustration shows the picotee edging, informal placement of florets on the stem and the ruffling.

In the following detailed description, color plate references are to the "Horticultural Colour Chart," by the British Colour Council. Where there are other references, the ordinary dictionary meanings of the terms are intended.

*The Plant*

Growth: Bloom spike height is 42 to 50 inches over-all. Propagation is slow; plants are among the first to die down in fall.

Blooming: Each spike opens from six to eight 3½-inch florets at one time. Successive blooms open, totalling an average of eighteen to twenty to each spike. The variety is a mid-season bloomer, blooming in 80 days from large bulbs.

Stems: Willowy; diameter at base is ⅓ inch.

Foliage: Normal; average leaf is 1 to 1½ inches wide and the plant foliage, excluding the flower spike, is 24 inches high. Plants turn brown early in the fall, but the bulbs are clean and healthy.

Corms: Smooth, round, red; thin, papery husk. Average diameter is 2 inches from adult plants. Flesh is slightly paler than Oxblood Red oo823/$_3$.

*The Flower*

Spike: Medium height; has sixteen to twenty buds of which two or three are open the first day, following which six to eight are open at one time.

Bud:

*Size.*—Opening buds are 2 inches long.

*Opening.*—Seven to eight show color at one time.

Flower:

*Arrangement.*—Florets are alternately placed on the spike and all face in the same direction.

*Size.*—Florets average 3½ to 4 inches in diameter. Upper blooms are progressively smaller.

*Form.*—The florets are triangular, recurved and ruffled.

*Keeping qualities.*—Opens well; keeps well.

Petals :

*Shape.*—Petals are elongated, ruffled, recurved and picoteed.

*Size.*—The outer petals are 1¾ inches across and the inner petals are 1¼ inches across.

*Aspect.*—Substance is average and the surface is smooth with ruffling at the edges.

*Fragrance.*—None.

*Color.*—The dominant color is Currant Red 821 shading to 821/$_3$. Upper petal is Blood Red 820/$_3$. Picotee edging is Chinese Yellow 606/2 and same color deep in the calyx.

Reproductive organs:

*Stamens.*—White with tints of Persian Rose 628/$_3$.

*Pistils.*—Persian Rose 628/$_1$.

*Comparisons*

My new variety resembles Atom (unpatented) more than any other variety, but differs from it principally as follows:

(1) My variety is larger and taller than Atom.
(2) My variety has more florets open at once.
(3) My variety has heavier substance.
(4) My variety is a deeper color than Atom.
(5) My variety has a more-double row of florets than Atom.

Having thus disclosed my invention, I claim:

The new and distinct variety of gladiolus plant, substantially as herein shown and described, characterized by its fine Chinese Yellow picotee edging on a deep, velvety red background, ruffled florets and heavy substance.

No references cited.